(12) United States Patent
Aslan et al.

(10) Patent No.: US 12,067,726 B2
(45) Date of Patent: Aug. 20, 2024

(54) RETINA IMAGE ANNOTATION, AND RELATED TRAINING METHODS AND IMAGE PROCESSING MODELS

(71) Applicant: Vestel Elektronik Sanayi ve Ticaret A.S., Manisa (TR)

(72) Inventors: Muhammet Aslan, Manisa (TR); Canan Asli Utine, Manisa (TR); Cihan Topal, Manisa (TR); Özlem Özden Zengin, Manisa (TR)

(73) Assignee: VESTEL ELEKTRONIK SANAYI VE TICARET A.S., Manisa (TR)

( * ) Notice: Subject to any disclaimer, the term of this patent is extended or adjusted under 35 U.S.C. 154(b) by 0 days.

(21) Appl. No.: 18/289,547

(22) PCT Filed: May 5, 2022

(86) PCT No.: PCT/EP2022/062189
§ 371 (c)(1),
(2) Date: Nov. 3, 2023

(87) PCT Pub. No.: WO2022/234035
PCT Pub. Date: Nov. 10, 2022

(65) Prior Publication Data
US 2024/0249415 A1  Jul. 25, 2024

(51) Int. Cl.
*G06K 9/00* (2022.01)
*G06T 7/00* (2017.01)
(Continued)

(52) U.S. Cl.
CPC .............. *G06T 7/11* (2017.01); *G06T 7/0014* (2013.01); *G06T 7/174* (2017.01); *G06T 7/70* (2017.01);
(Continued)

(58) Field of Classification Search
CPC ............................................. G06T 2207/30041
See application file for complete search history.

(56) References Cited

U.S. PATENT DOCUMENTS

2018/0315193 A1\* 11/2018 Paschalakis .............. G06T 7/11
2020/0125598 A1\* 4/2020 Trilisky ................ G06F 16/535
(Continued)

FOREIGN PATENT DOCUMENTS

| CN | 111696100 A | 9/2020 |
|---|---|---|
| WO | 2019210079 A1 | 10/2019 |
| WO | 2020056454 A1 | 3/2020 |

OTHER PUBLICATIONS

International Search Report and Written Opinion of the International Searching Authority for International Application No. PCT/EP2022/062189 dated Sep. 19, 2022 (14 pages).
(Continued)

*Primary Examiner* — Hadi Akhavannik
(74) *Attorney, Agent, or Firm* — Jorge Miguel Hernandez; James R. Gourley; Carstens, Allen & Gourley, LLP (57) ABSTRACT

A computer-implemented method of annotating conventional retina images, the method comprising: receiving a conventional image of a retina, the conventional retina image captured using an image capture device; receiving an associated crosssectional image of said retina, the cross-sectional image captured using a crosssectional imaging system; determining a disease location in an image plane of the cross-sectional image; and generating annotation data for annotating the disease location in an image plane of the conventional image, by projecting the disease location from the image plane of the cross-sectional image into to the image plane of the conventional image, based on a known mapping between the cross-sectional image and the conventional image.

15 Claims, 9 Drawing Sheets

(51) Int. Cl.
  *G06T 7/11* (2017.01)
  *G06T 7/174* (2017.01)
  *G06T 7/70* (2017.01)
(52) U.S. Cl.
  CPC .............. *G06T 2207/10101* (2013.01); *G06T 2207/20081* (2013.01); *G06T 2207/30041* (2013.01)

(56) References Cited

U.S. PATENT DOCUMENTS

| | | | |
|---|---|---|---|
| 2020/0372632 A1* | 11/2020 | Chauhan | A61B 3/0025 |
| 2022/0092780 A1* | 3/2022 | Chauhan | G06T 7/0012 |
| 2022/0125948 A1* | 4/2022 | Kay | C07K 14/4702 |
| 2022/0328189 A1* | 10/2022 | Zhou | G06V 10/82 |

OTHER PUBLICATIONS

Varadarajan, Avinash, et al., "Predicting optical coheence tomography-derived diabetic macular edema grades from fundus photographs using deep learning," Nature Communications, vol. 11, No. 1, Jan. 8, 2020 (Jan. 8, 2020) (8 pages).

* cited by examiner

RETINA IMAGE ANNOTATION, AND RELATED TRAINING METHODS AND IMAGE PROCESSING MODELS

CROSS REFERENCE TO RELATED APPLICATION

This application is a US 371 application from PCT/EP2022/062189 entitled "Retina Image Annotation, and Related Training Methods and Image Processing Models" filed on May 5, 2022 and published as WO 2022/234035 on Nov. 10, 2022. The technical disclosures of every application and publication listed in this paragraph are hereby incorporated herein by reference.

TECHNICAL FIELD

The present disclosure relates to retina image annotation, and related image training methods and image processing models.

BACKGROUND

The current practice in ophthalmology exploits fundus images for diagnosis of a number of diseases, as well as patient follow-up, and utilizes optical coherence tomography (OCT) images for estimating the disease severity and planning treatment. Fundus photography is cheaper and more widely available than OCT.

Fundus images are obtained by photographing the rear of an eye using a specialised fundus camera. Ophthalmologists and other trained medical professionals may be trained to use fundus images to identify many eye conditions and/or diseases, in particular posterior segment disorders such as age-related macular degeneration, diabetic retinopathy and glaucoma. Early diagnosis of such diseases is important to minimise vision loss. Fundus images may also be used to monitor disease progression. Fundus imaging can be carried out using low-cost and/or portable equipment and therefore can be used for diagnosis of such eye disorders by ophthalmologists or other medical professionals in various outpatient settings.

Optical coherence tomography provides cross-sectional layered views of the fundus (rear of the eye). OCT is often used in monitoring and in determining treatment for posterior segment eye disorders mentioned above. However, a limitation of OCT is that the equipment used to capture these images is expensive and immobile, and therefore is typically only located in hospitals. OCT therefore typically is used in identifying treatment plans and other periodic monitoring post-diagnosis.

Recently, methods have been developed to identify indicators of eye disease automatically using artificial neural networks. Existing methods use one of fundus images or OCT image as input and output a prediction for the given fundus or OCT image. Specially-trained ophthalmologists can also manually detect indicators of eye disorders by analysing OCT data.

SUMMARY

In one example implementation, the present architecture provides a method of annotating fundus images based on OCT data. The annotated fundus images may then be used to train a machine learning component to classify retinal images based on fundus data only. This annotation of training data teaches the system to discover some previously unknown or unnoticed visual features that were too subtle to be recognized, or to be observed by human perception. This is an improvement over existing methods exploiting only fundus or OCT data respectively, as the model learns to identify visual features in fundus images which may not be visible to a manual annotator, based on previous training alongside OCT data. Images annotated using the present techniques can be used to train an image processing to more accurately detect disease patterns in fundus images (captured with low-cost fundus imaging equipment, without requiring expensive OCT equipment), and potentially even disease patterns that would not be visible to a human or would require a high level of human expertise to spot. Benefits of the present techniques therefore include increased disease detection capabilities using low-cost imaging equipment, and de-skilling of the disease detection process. This enables fundus data to be used in treatment and follow-up decisions where there are limitations on access to OCT data, for example due to cost. Funds images and OCT scans are referred to by way of example, but the techniques can be applied to other forms of imaging/scanning technology.

According to a first aspect disclosed herein, there is provided a computer-implemented method of annotating conventional retina images, the method comprising: receiving a conventional image of a retina, the conventional retina image captured using an image capture device; receiving an associated cross-sectional image of said retina, the cross-sectional image captured using a cross-sectional imaging system; determining a disease location in an image plane of the cross-sectional image; and generating annotation data for annotating the disease location in an image plane of the conventional image, by projecting the disease location from the image plane of the cross-sectional image into to the image plane of the conventional image, based on a known mapping between the cross-sectional image and the conventional image.

The image plane of the cross-sectional image may lie substantially parallel to the image plane of the conventional image, such that the cross sectional image maps to a scan line in the image plane of the conventional image.

Multiple cross-sectional images associated with the conventional retina image may be received, and multiple disease locations are determined in respective image planes of the cross-sectional images and projected into the image plane of the conventional image to generate the annotation data.

The annotation data may be generated via interpolation of the projected disease locations within the image plane of the conventional image.

The multiple cross-sectional images may correspond to multiple scan lines in the image plane of the conventional image, and the annotation data may be generated by interpolating the projected disease locations within one or more regions separating the scan lines.

The or each disease location may be determined in the image plane of the cross-sectional image: via automated image recognition applied to the cross-sectional image, via manual annotation applied to the cross-sectional image, or via a combination of automated image recognition and manual annotation.

The annotation data may be generated in the form of a segmentation mask.

The segmentation mask may assign a severity level to each of at least some pixels of the conventional image, based on at least one of: a severity level(s) assigned to the disease location(s) in the cross-sectional image, and a depth of the disease location(s) within or behind the retina.

The conventional image may be a fundus image, the image capture device being a fundus camera.

The cross sectional image may be an optical coherence tomography (OCT) image, the cross-sectional imaging system being an OCT imaging system.

The multiple disease locations may be determined in the image plane of the cross-sectional image, and a geometric voting algorithm may be applied to the multiple disease locations to generate the annotation data based on at least one of: a severity level assigned to each disease location in the cross-sectional image, and a depth of each disease location within or behind the retina.

The method may be applied to multiple conventional retina images and respective associated cross-sectional images, to generate respective annotation data for the multiple conventional retina images, wherein the multiple conventional retina images and their annotation data are used to train an image processing model to identify disease regions in conventional retina images, the multiple conventional retina images used as training inputs and their respective annotation data providing training ground truth, wherein the training inputs do not include the cross-sectional images.

The training inputs may additionally comprise associated patient data.

According to another aspect disclosed herein, there is provided an image processing system comprising: an input configured to receive a conventional retina image; and one or more processors configured to apply a trained image processing model to the conventional retina image, in order to identify at least one disease location therein, the image processing model trained in accordance with any training method disclosed herein.

According to another aspect disclosed herein, there is provided a computer program embodying an image processing model, trained in accordance with any training method disclosed herein.

BRIEF DESCRIPTION OF THE DRAWINGS

To assist understanding of the present disclosure and to show how embodiments may be put into effect, reference is made by way of example to the accompanying drawings in which.

To assist understanding of the present disclosure, certain figures are provided in colour format.

DETAILED DESCRIPTION

Described below is an artificial intelligence system to extract more useful information from fundus images. This system is trained based on a comprehensive data set consisting of pairs of images, each pair comprising a fundus image and a corresponding optical coherence tomography (OCT) scan. The dataset is used to identify visual cues in fundus images by correlating fundus images with OCT data. An annotated set of fundus images may be obtained by applying the correlation with OCT data, with the annotations identifying pixels of the fundus images corresponding to areas of interest in the corresponding OCT scans. While a human annotator may not be able to identify certain visual indicators of a fundus image that correspond to a feature of interest on an OCT image, supplying the pair to an artificial intelligence algorithm allows the system to learn how OCT features appear in the fundus image, even if these visual features are undetectable to the human eye. Each fundus image of the fundus-OCT pair may be annotated based on this correlation. The annotated fundus images are then used to train an AI algorithm to detect visual features of interest for unannotated fundus images only.

Figure 1A:
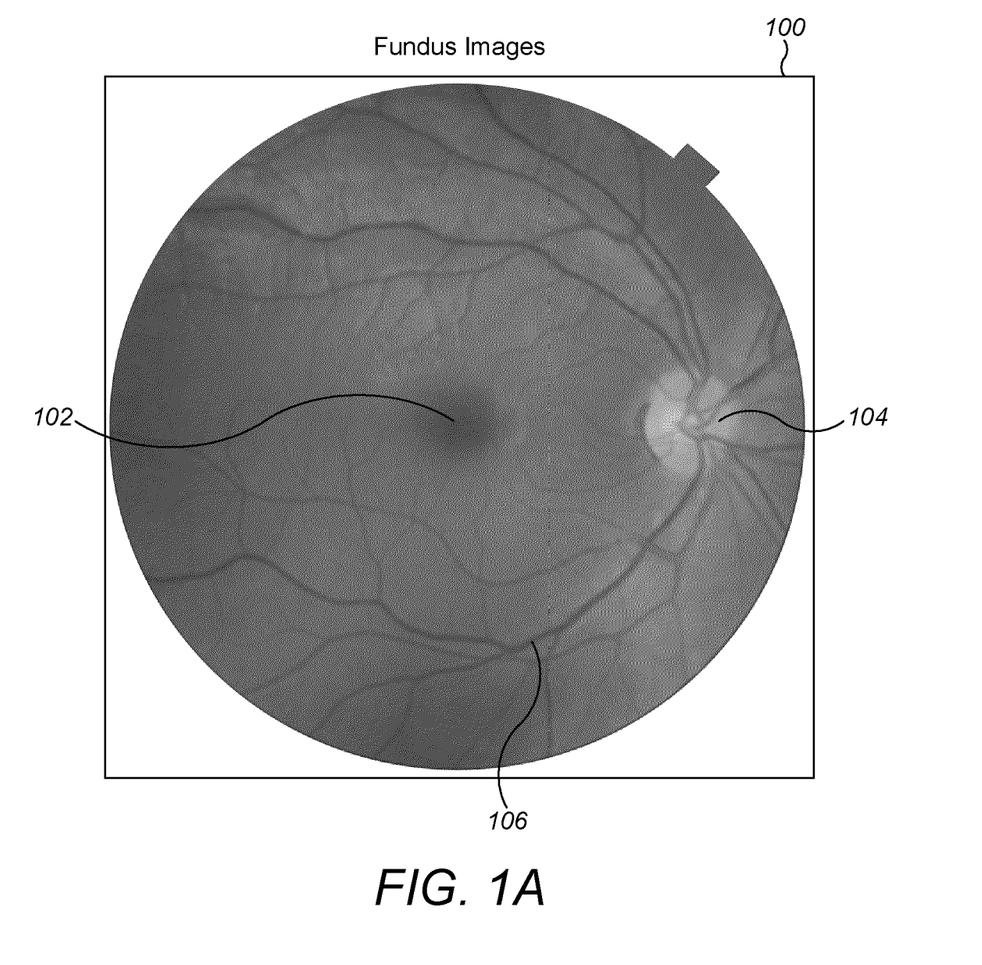
FIG. 1A shows schematically a fundus image.

FIG. 1A shows an example of a fundus image. A fundus image is a conventional camera image showing the rear (fundus) of an eye. The fundus image 100 shown in FIG. 1A shows a fundus with no sign of disease. Fundus images are typically captured with specialised camera equipment comprising a microscope attached to a flash-enabled camera. Low-cost and portable fundus cameras may be used in a variety of settings. The fundus image 100 shown in FIG. 1A shows a 2D view of the back of the eye.

The retina comprises a number of layers, some of which are semi-transparent. The fundus image 100 is a 2D image and therefore does not provide any depth information for any irregularities or features of interest in the image. The image 100 shows the macula 102 in the centre of the image, the optic disc to the right, and blood vessels 106 of the eye. Retinal abnormalities visible in a fundus image 100 may be used by a trained ophthalmologist or other medical professional to diagnose a number of eye-related diseases or conditions affecting the back of the eye, including age-related macular degeneration, diabetic retinopathy, and glaucoma. However, development of treatment plans and ongoing monitoring may require techniques to identify the depth of the abnormality.

Figure 1B:
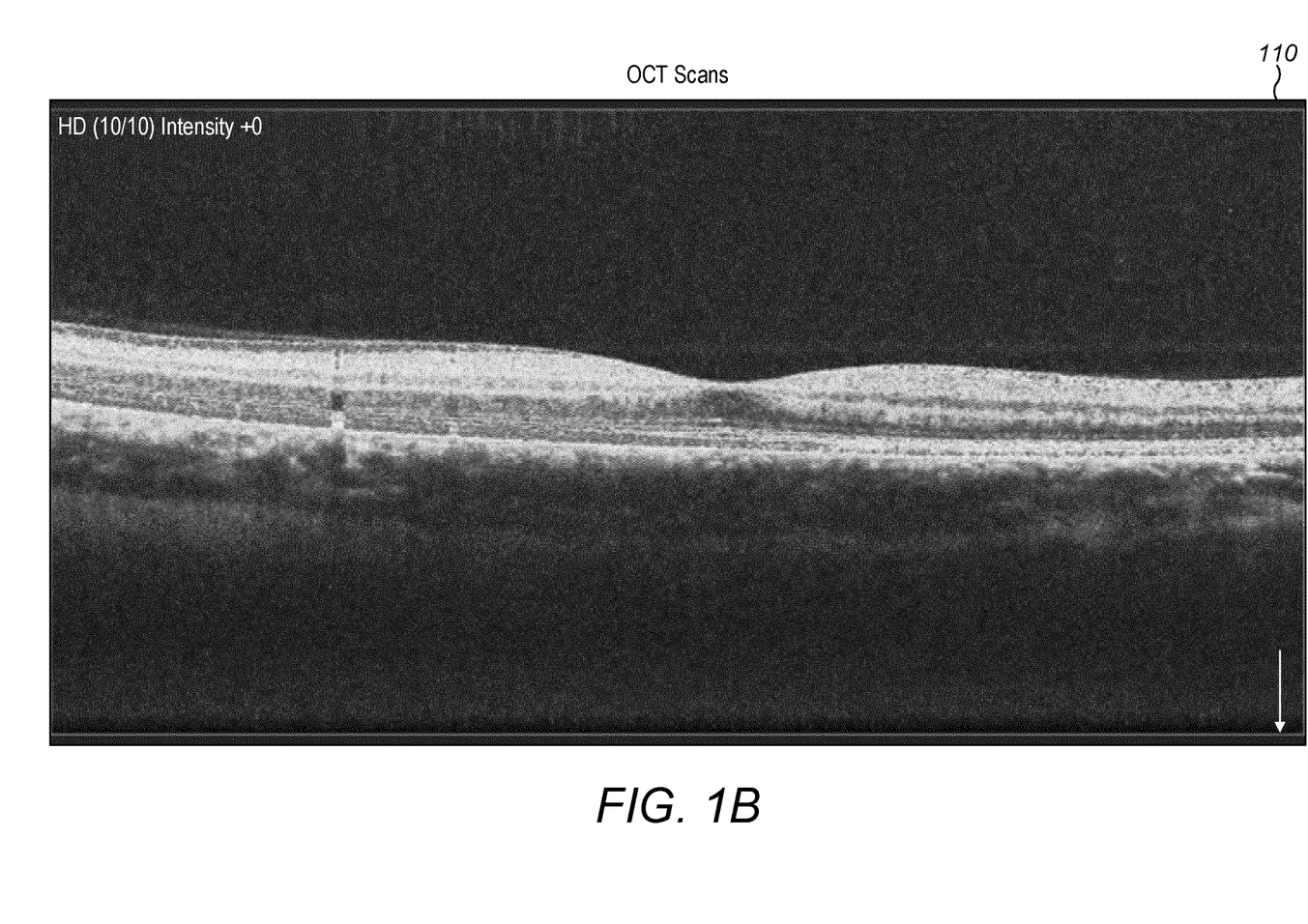
FIG. 1B shows schematically an OCT scan of a cross section of the fundus.

FIG. 1B shows an example of an OCT scan 110 of a retina. Each OCT scan represents a single horizontal cross-section of the back of the eye at a given height. A single OCT scan 110 corresponds to a horizontal line of a fundus image 100. The OCT scan captures depth information of the fundus. As shown in FIG. 1B, different layers of the retina are visible and may appear as different colours or shades in an OCT scan. Identifying the depth of retinal abnormalities is important in the diagnosis and treatment of eye diseases such as those mentioned above. Equipment for capturing OCT scans is expensive and generally not portable. Typically OCTs are employed in ophthalmology only in hospital settings, and are more often used to aid in treatment planning for diagnosed posterior segment diseases mentioned above than as a diagnostic tool.

For the artificial intelligence system described herein, a comprehensive dataset comprising both fundus images and corresponding OCT data is used.

Figure 2:
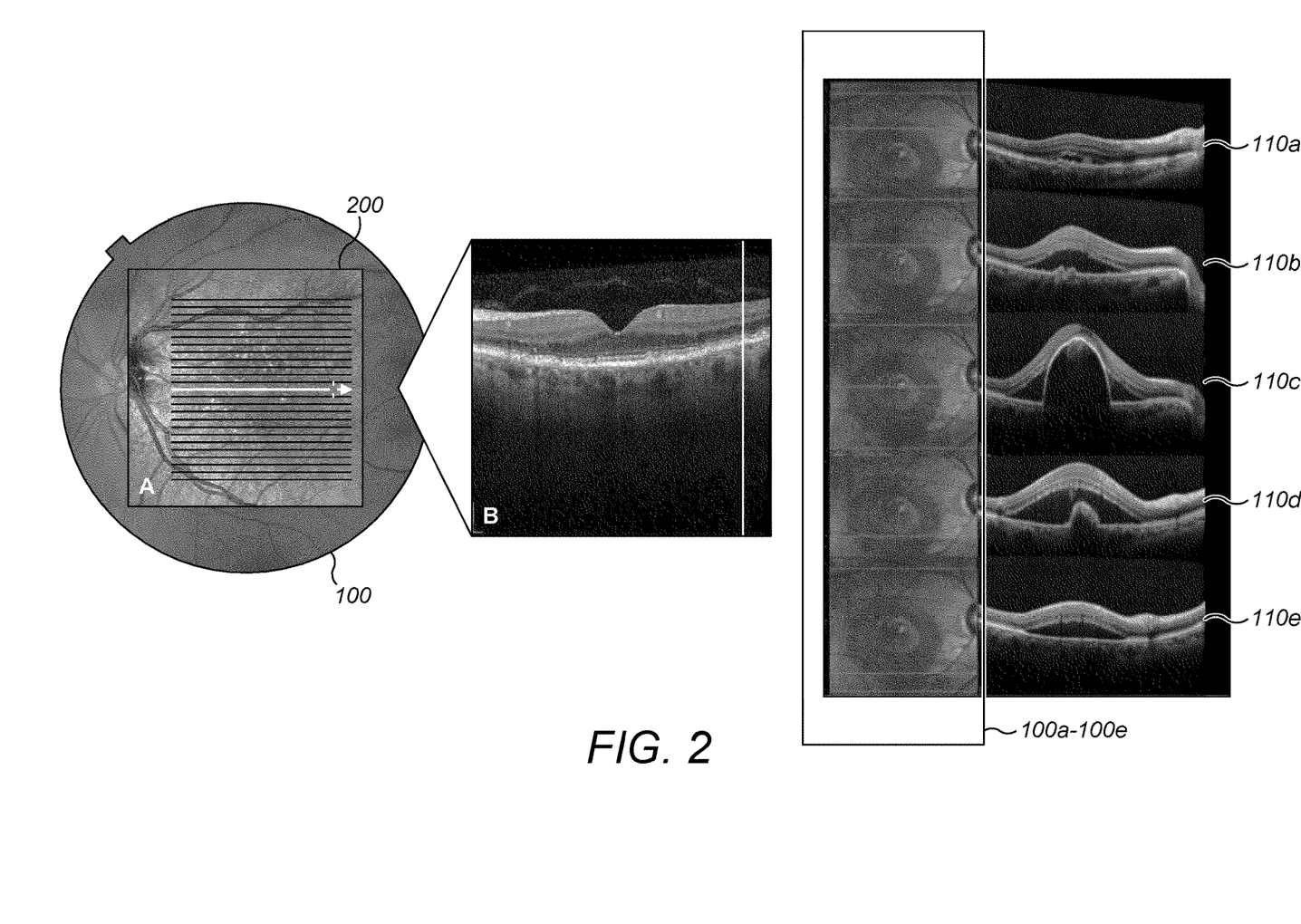
FIG. 2 shows schematically a series of OCT scan cross sections taken at various heights of a 2D fundus image.

FIG. 2 shows the association between a single fundus image 100 and a series of OCT scans 110a-110e. A series of OCT scans may be taken across the centre of the fundus image 100, as shown by the area 200 of the fundus image. The OCT images may focus on a particular region of the fundus, in this example the centre. Each OCT scan corresponds to one of the vertical lines shown in the area 200. An example OCT scan 110 is shown which corresponds to the bright green line in the centre of the fundus image. In the OCT scan 110, the layers of the fundus are visible as different shades. The retina comprises a series of semi-transparent layers of neurons and below these is a pigmented layer. The choroid, which is the vascular layer of the eye, lies below this pigmented layer. Layering of the retina is shown in image 202. Each layer of the retina may be identified from an OCT scan by a trained professional such as an ophthalmologist.

Each horizontal line shown in image 200 corresponds with a different OCT scan. On the right of FIG. 2, a series of OCT scans 110a-110e, each taken at a different vertical height. A green line is shown in each fundus image 100a-100e on the left showing the height of the given scan within the fundus. As shown, each scan shows a different profile of the retinal tissue. Any abnormalities identified in the OCT scans may be identified with the given vertical height as well as the depth and the horizontal position given by the OCT scan itself. Abnormalities may be identified across multiple spans based on their appearance and position in the scans. Abnormalities may be identified manually by a domain expert such as a trained ophthalmologist, or it may be identified automatically, for example by using a trained machine learning model.

The system described herein uses identified features of OCT scans, such as abnormalities, to train a fundus classifier. Annotation of OCT scans is described in more detail below.

The system described herein is used to train a fundus classifier that applies classification to each pixel of the input image. In other words, the fundus classifier segments the image into sets of pixels corresponding to multiple classes.

Figure 3:
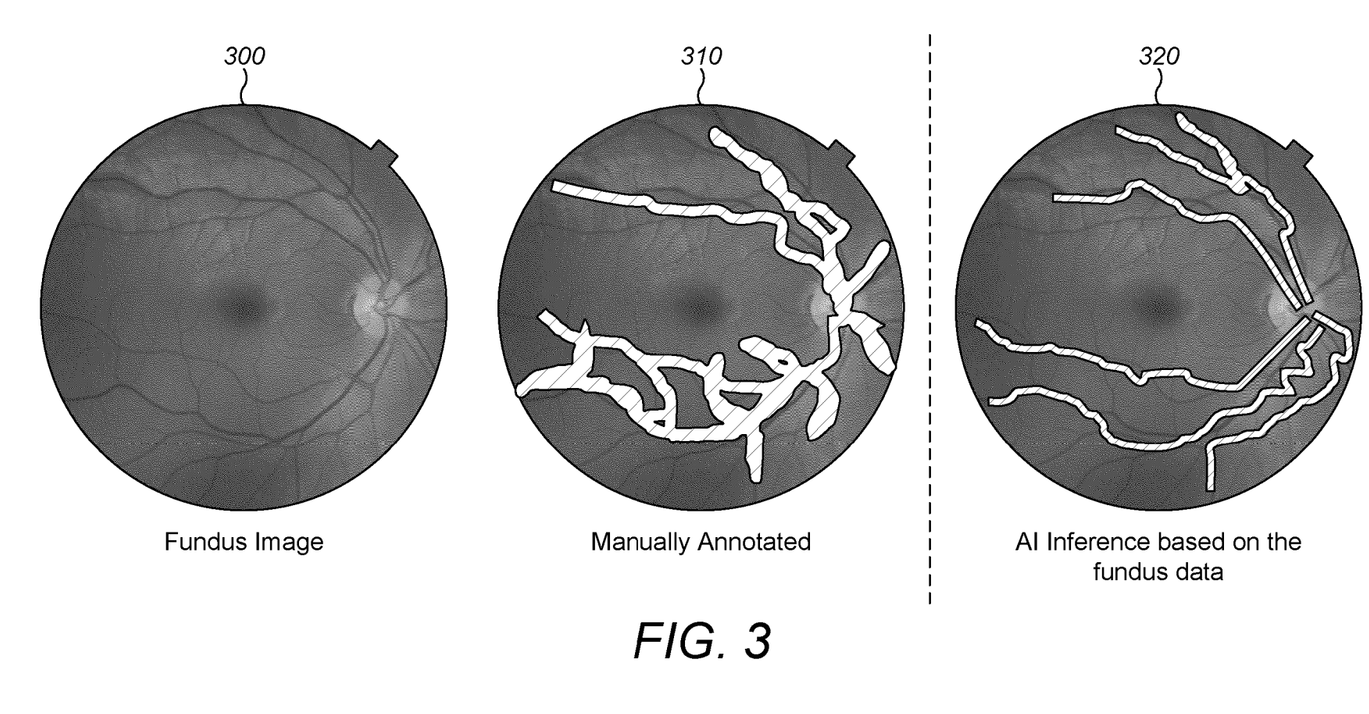
FIG. 3 shows schematically an input and output of an example state-of-the-art fundus image segmentation method.

FIG. 3 shows an example of the input data and results of a state-of-the-art classifier/segmentation method for fundus images. A domain expert, as mentioned above, may identify areas of the fundus image typically visible to a domain expert. In the example of FIG. 3, a training fundus image 300 is of a healthy eye. In this example, the classifier may be used to detect the blood vessels visible in the image. Image 310 shows an example of a manual annotation provided by a domain expert which marks out the blood vessels of the fundus visible in the training image 300. A machine learning model, for example a convolutional neural network may be trained on pairs of fundus training images 300 and manual annotations 310.

Convolutional neural networks (CNNs) are commonly used in image processing tasks such as image segmentation. CNNs comprise a number of layers, including convolutional layers consisting of a set of kernels which are convolved across an input volume, where the input volume may be a 2D or 3D array representing an image. For example, a colour image may be represented by three colour channels, each comprising a 2D M×N array of pixel values, such that the input volume is a M×N×3 tensor. CNNs also include pooling layers which 'downsample' an input to a lower dimensional array, and layers applying nonlinearities such as ReLU. Each layer outputs a volume of feature arrays. The original resolution of the input image may be restored to the output by applying upsampling layers if, for example, the desired output of the network is an annotated version of the input image.

In training, the convolutional neural network is first initialised with a set of weights. The input training image 300 is processed by the network which predicts a label for each pixel of the input image. In training, a loss function is used to assess the labels predicted by the network against the manual annotations 310 provided for the given input image. The weights of the network are updated such that the network predictions are close to the manually annotated examples for a training set of multiple annotated fundus images. A variety of loss functions and specific architectures may be defined to achieve the training goal of predicting accurate pixel labels.

Once the network is trained, it may be applied in an inference stage. At inference, a fundus image 100 without any manual annotation is input to the network, which applies its trained weights and outputs a label for each pixel of the image, for example identifying certain pixels of the image as blood vessels. An example output 320 is shown in FIG. 3. The predicted areas of the image corresponding to blood vessels is shown in purple. The example of FIG. 3 shows the inference output applied to the same image 300 shown for training. However, in inference, the network is generally applied to fundus images which have not been seen in training.

A system will now be described which enables annotation of fundus images based on OCT data. This allows training of a fundus classifier of the type described above, without the limitation of the annotated training data being based only on visual features observable by a human expert. The method described below enables a computer system to learn subtle visual features of a fundus image which tend to correspond with particular features identifiable in an OCT scan. By annotating based on the OCT data, the resulting fundus segmentation network aims to extract information from 2D fundus images which can be used in diagnosis, follow-up monitoring, and treatment of eye conditions.

Figure 4:
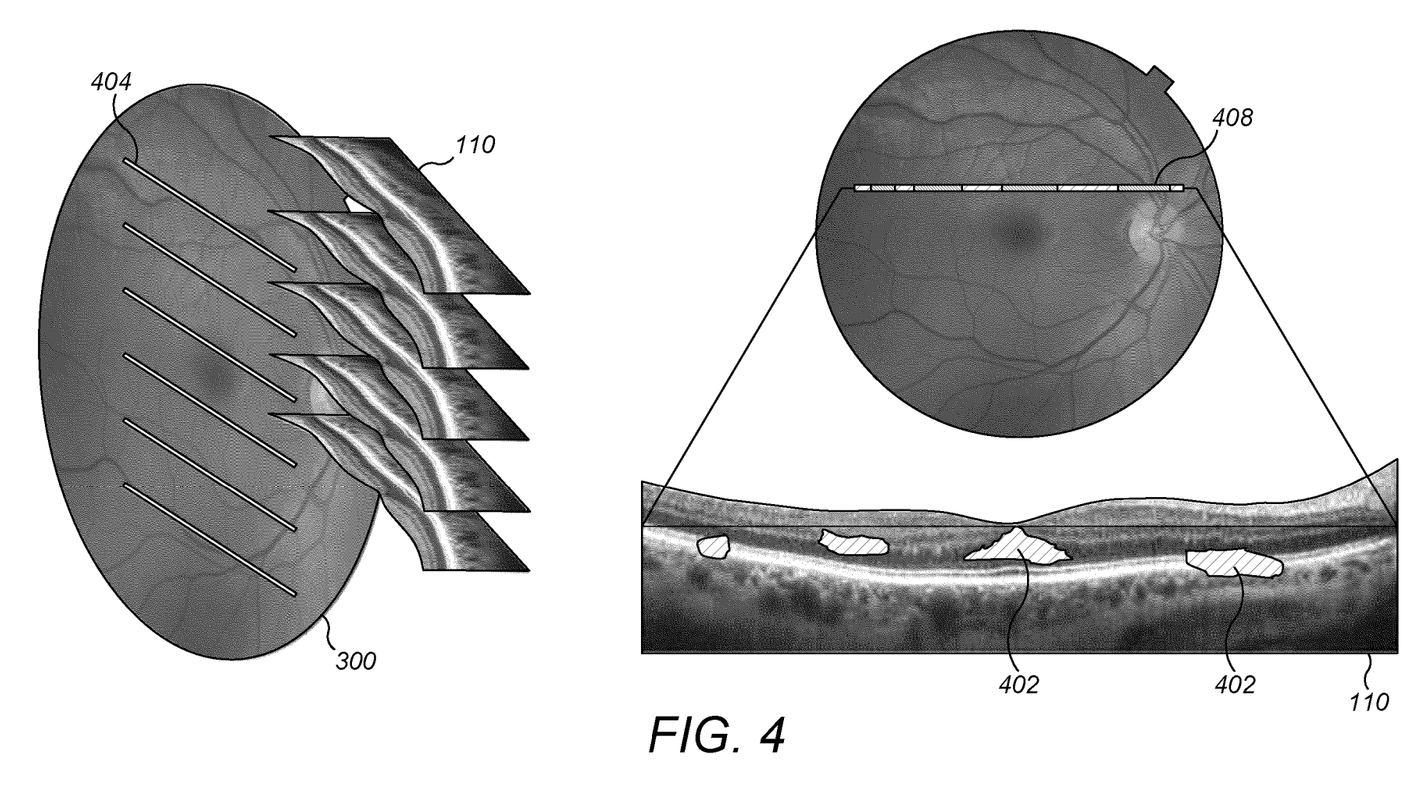
FIG. 4 shows schematically how pixels of a fundus image may be annotated based on OCT data.

FIG. 4 shows how annotations may be applied to a fundus image based on an OCT image for which areas of interest have been annotated. As mentioned above, an OCT image may itself be automatically annotated by applying a trained artificial intelligence model, described later with reference to FIG. 7, or may be annotated manually by a domain expert trained in analysing OCT images. The OCT image 110 in FIG. 4 shows a number of annotated areas 402, highlighted in green. These may, for example, represent abnormalities in the fundus indicative of disease, or other features of interest. Annotations may comprise labels identifying a type of abnormality, and/or other relevant features, such as a severity. Severities may be determined by the automatic or manual annotator based on training data and domain expertise, respectively.

As shown on the left of FIG. 4, each OCT image corresponds with a cross section of a 2D fundus image, represented by a single line 404 on the training fundus image. In order to annotate the fundus image in 2D, the annotations of the OCT scans must be projected onto the plane of the fundus image 300. This is shown on the right hand side of FIG. 4. A geometric voting algorithm is described in more detail below with reference to FIG. 5, which may be used to determine which pixels of the original fundus image should be annotated based on the annotated segments of the OCT image. The corresponding annotations are shown on the line of the fundus image as red segments 408. Once the annotations 408 have been determined along the lines corresponding to the OCT scans, the remaining pixels of the fundus image, i.e. pixels lying between OCT scans, may be annotated by applying an interpolation technique to the annotated sets of pixels.

Figure 5:
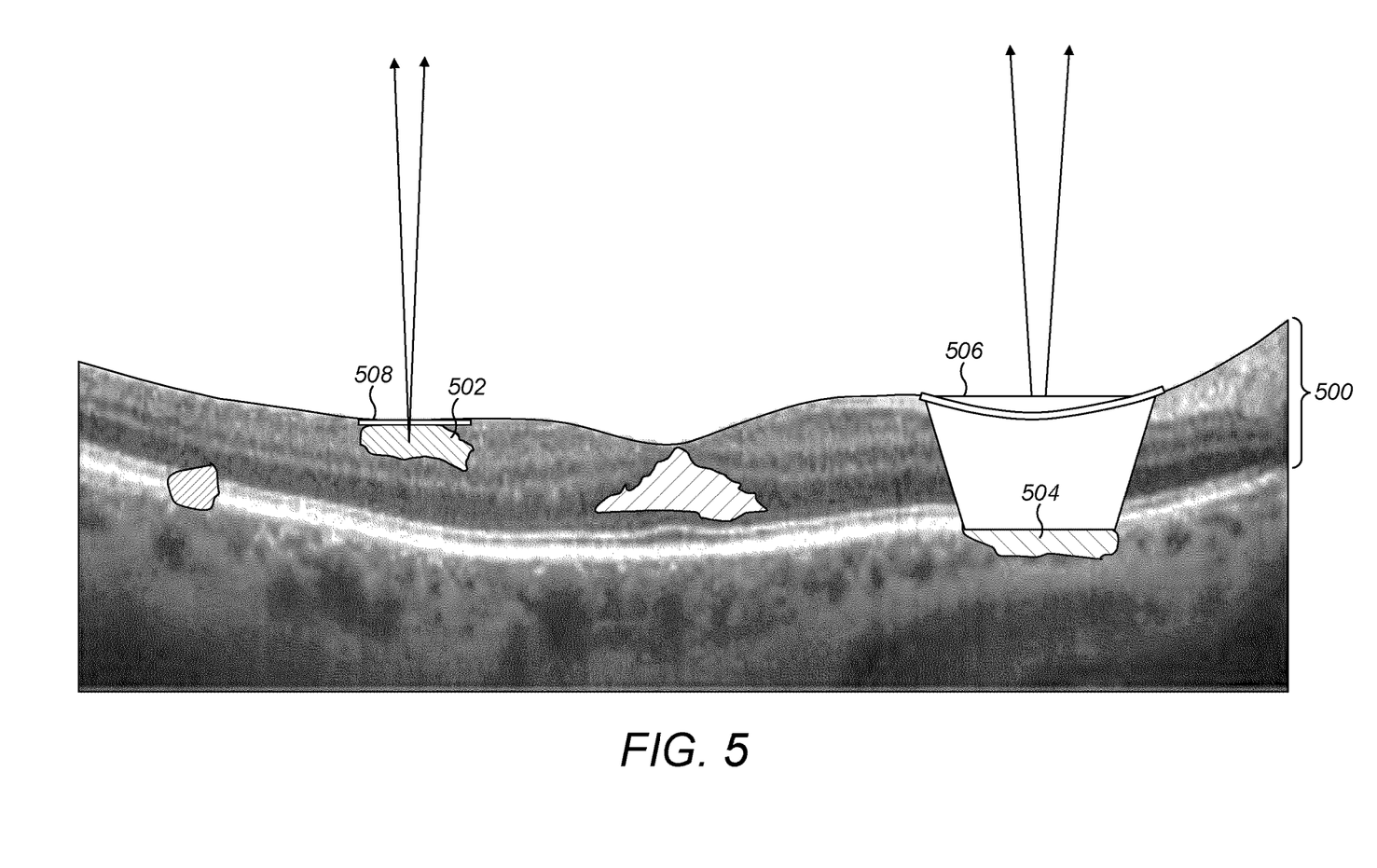
FIG. 5 shows schematically a geometric voting algorithm applied to an annotated OCT scan.

FIG. 5 shows a Geometric Voting Algorithm applied to project annotations of an OCT scan image to the top layer of the retina, and map this projection onto the corresponding line of a fundus image. As described above, the retina comprises a series of transparent or semi-transparent layers of tissue, as shown by the area in FIG. 4. The annotation of the fundus image 300 aims to associate even small or subtle visible features of the fundus with features of the OCT scan 110.

It is important that annotations of the OCT image are mapped onto features of the fundus image that are actually detectable by a computer network, although they do not need to be visible to the human eye. The depth of the OCT features may therefore taken into account, since features appearing in deeper layers of the retina are less likely to appear in a fundus image and therefore annotating the corresponding area of the fundus image is not helpful for training a segmentation network for fundus images.

A severity of the OCT annotations may also be used by the voting scheme to determine the shape of the abnormality or visual feature identified in the OCT as it appears in the image plane of the fundus image. For example, it is important to flag abnormalities which are considered severe in an OCT image, so that any visual indicator that may exist in the fundus image may be identified by the network, therefore making the network sensitive to severe indicators of disease even if not highly visible.

Geometric voting algorithms have previously been applied in the field of astronomy in order to track stars. This algorithm is not described in detail herein. The geometry of the retinal layers may be used, along with knowledge of the visibility of features at various depths of the retina in order to determine the shape of the corresponding visual feature as it appears in the training fundus image 300. This is shown for the green and blue annotations of the OCT scan in FIG. 5.

Figure 6:
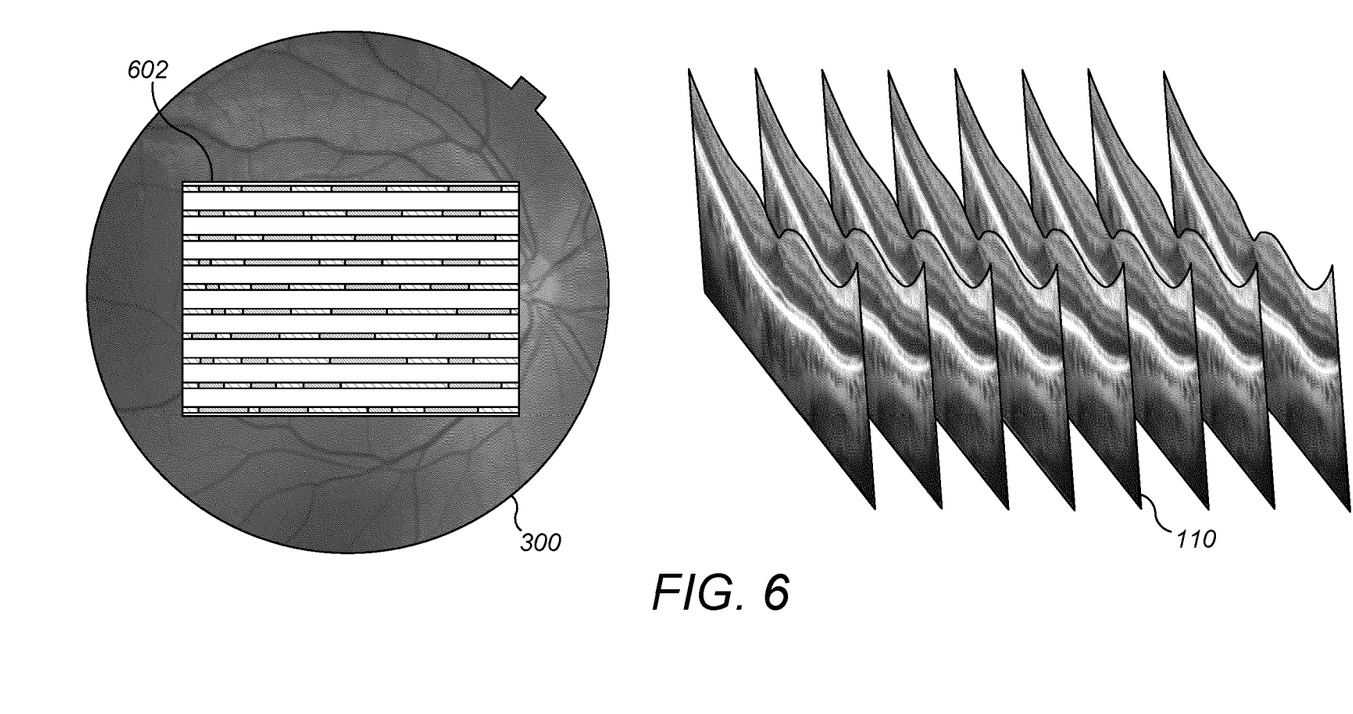
FIG. 6 shows how dense registration may be applied to a partially annotated fundus image.

Once the pixels of the fundus image corresponding to the OCT scans have been annotated, remaining pixels of the fundus image 300 may be annotated using an interpolation. Between eight and one hundred OCT scans may be collected for a single fundus image, providing a subset of annotated pixels for the fundus image. Dense registration may be used to interpolate the annotation values for the pixels of each line 404 to remaining pixels of the image to obtain a continuous area of annotated pixels 602. This is shown in FIG. 6.

Figure 7:
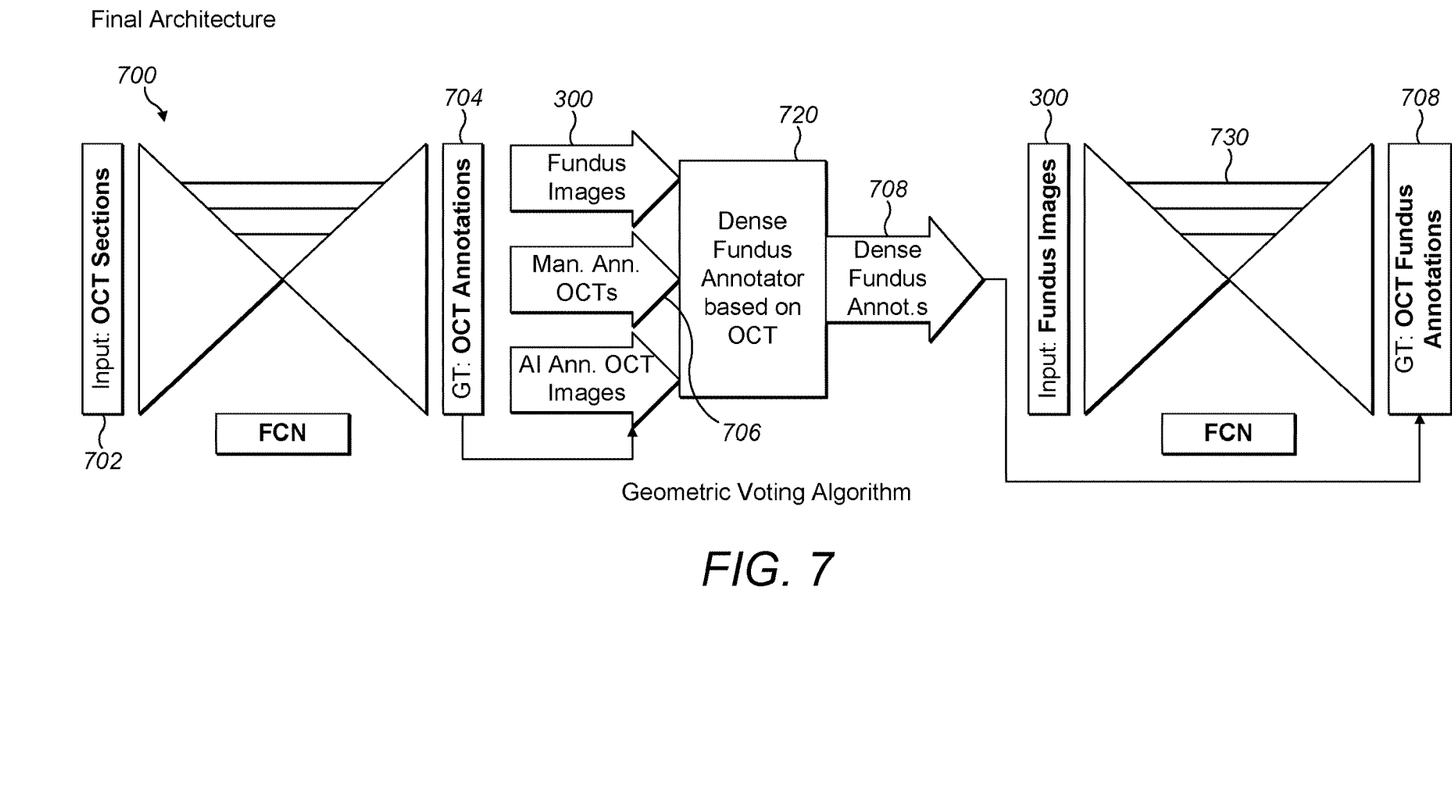
FIG. 7 shows an architecture for generating annotated fundus images and training a fundus image segmentation network.

FIG. 7 shows an example architecture comprising a pipeline for generating annotated fundus images and a convolutional neural network which may be trained based on the generated fundus annotations to apply pixel-wise classification to the fundus images based on learned relationships with OCT data.

Automatic annotation of OCT scans may be carried out by a trained convolutional neural network 700 to generate a set of 'ground truth' automatic OCT annotations 704. A human annotator with domain expertise may also analyse the OCT scans for each fundus training image 300 to generate a set of manual 'ground truth' annotated OCT scans 706.

Each of the training fundus images 300, as well as the set of manually annotated OCT scans 706, and automatically annotated OCT scans 704, are input to a dense fundus annotator which annotates the fundus images based on the OCT annotations using a geometric voting algorithm to apply pixel annotations along the lines 404 of the input fundus image 300, and dense registration to determine pixel annotations for remaining pixels of the image. The annotator 720 then outputs the dense 'ground truth' fundus annotations which may be used along with the unannotated training images 300 to train a segmentation network 730, which may take the form of a convolutional neural network, and which is trained as described earlier with reference to FIG. 3.

Figure 8:
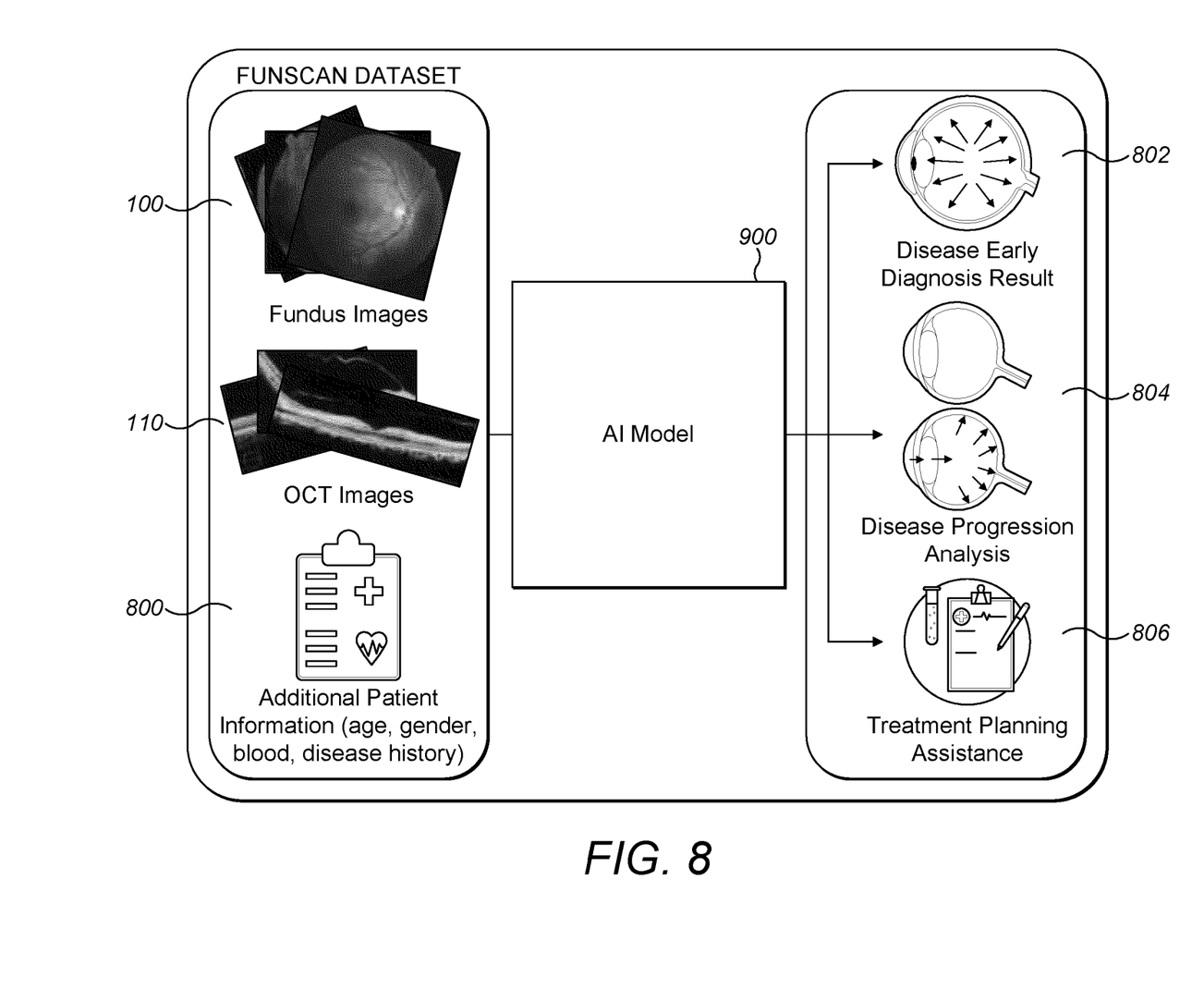
FIG. 8 shows an example input dataset and output of an artificial intelligence model trained on annotated fundus images.

As described above, the methods herein allow conventional fundus images to be annotated to train a model which can make OCT-based predictions for inputs comprising fundus image alone. However, models of diagnosis and treatment may be further improved by introducing further input data, such as patient information, including age, gender, disease history, which can be strong indicators of risk, and which may influence treatment options in case of disease. FIG. 8 shows an example of the possible inputs and outputs of an artificial intelligence model which may be at least partially trained according to the methods described above. Input datasets can include OCT images 110 as well as corresponding patient information 800 and fundus images. OCT images, as described above, are used in annotating a set of fundus images to incorporate or recognise features o OCT images not obvious in fundus data. Additional patient data may be used either in the annotation stage, in order to learn correlations between patient attributes and corresponding fundus images, but may also be provided to the image segmentation network in order to help in predicting, for example, the risk or severity of identified abnormalities or other visual features of the fundus.

The output of the network described in FIG. 7 is a set of annotated fundus images, with pixels classified according to one or more labels, identifying or classifying the severity of possible diseases. This data may be further processed by the model 900, comprising at least the network components described in FIG. 7, to determine or aid a human expert in determining outputs such as a diagnosis result 802, a progression analysis 804, or data for a treatment plan 806.

It will be appreciated that the components of FIGS. 7 and 8 are functional components implemented in a process or processing circuitry. The training method described above is a computer-implemented method that is implemented using the same. It will be understood that the processor or processing system or circuitry referred to herein may in practice be provided by a single chip or integrated circuit or plural chips or integrated circuits, optionally provided as a chipset, an application-specific integrated circuit (ASIC), field-programmable gate array (FPGA), digital signal processor (DSP), graphics processing units (GPUs), etc. The chip or chips may comprise circuitry (as well as possibly firmware) for embodying at least one or more of a data processor or processors, a digital signal processor or processors, baseband circuitry and radio frequency circuitry, which are configurable so as to operate in accordance with the exemplary embodiments. In this regard, the exemplary embodiments may be implemented at least in part by computer software stored in (non-transitory) memory and executable by the processor, or by hardware, or by a combination of tangibly stored software and hardware (and tangibly stored firmware).

Reference is made herein to data storage for storing data. This may be provided by a single device or by plural devices. Suitable devices include for example a hard disk and non-volatile semiconductor memory (including for example a solid-state drive or SSD).

Although at least some aspects of the embodiments described herein with reference to the drawings comprise computer processes performed in processing systems or processors, the invention also extends to computer programs, particularly computer programs on or in a carrier, adapted for putting the invention into practice. The program may be in the form of non-transitory source code, object code, a code intermediate source and object code such as in partially compiled form, or in any other non-transitory form suitable for use in the implementation of processes according to the invention. The carrier may be any entity or device capable of carrying the program. For example, the carrier may comprise a storage medium, such as a solid-state drive (SSD) or other semiconductor-based RAM; a ROM, for example a CD ROM or a semiconductor ROM; a magnetic recording medium, for example a floppy disk or hard disk; optical memory devices in general; etc.

The examples described herein are to be understood as illustrative examples of embodiments of the invention. Further embodiments and examples are envisaged. Any feature described in relation to any one example or embodiment may be used alone or in combination with other features. In addition, any feature described in relation to any one example or embodiment may also be used in combination with one or more features of any other of the examples or embodiments, or any combination of any other of the examples or embodiments. Furthermore, equivalents and modifications not described herein may also be employed within the scope of the invention, which is defined in the claims.

The invention claimed is:

1. A computer-implemented method of annotating conventional retina images, the method comprising:
   receiving a conventional image of a retina, the conventional retina image captured using an image capture device;
   receiving an associated cross-sectional image of said retina, the cross-sectional image captured using a cross-sectional imaging system;
   determining a disease location in an image plane of the cross-sectional image; and
   generating annotation data for annotating the disease location in an image plane of the conventional image, by projecting the disease location from the image plane of the cross-sectional image into to the image plane of the conventional image, based on a known mapping between the cross-sectional image and the conventional image.

2. The method of claim 1, wherein the image plane of the cross-sectional image lies substantially perpendicular to the image plane of the conventional image, such that the cross sectional image maps to a scan line in the image plane of the conventional image, the disease location projected onto the scan line.

3. The method of claim 1, wherein multiple cross-sectional images associated with the conventional retina image are received, and multiple disease locations are determined in respective image planes of the cross-sectional images and projected into the image plane of the conventional image to generate the annotation data.

4. The method of claim 3, wherein the annotation data is generated via interpolation of the projected disease locations within the image plane of the conventional image.

5. The method of claim 4, wherein the multiple cross-sectional images correspond to multiple scan lines in the image plane of the conventional image, and the annotation data is generated by interpolating the projected disease locations within one or more regions separating the scan lines.

6. The method of claim 1, wherein the or each disease location is determined in the image plane of the cross-sectional image:
   via automated image recognition applied to the cross-sectional image,
   via manual annotation applied to the cross-sectional image, or
   via a combination of automated image recognition and manual annotation.

7. The method of claim 1, wherein the annotation data is generated in the form of a segmentation mask.

8. The method of claim 1, wherein the segmentation mask assigns a severity level to each of at least some pixels of the conventional image, based on at least one of: a severity level(s) assigned to the disease location(s) in the cross-sectional image, and a depth of the disease location(s) within or behind the retina.

9. The method of claim 1, wherein the conventional image is a fundus image, the image capture device being a fundus camera.

10. The method of claim 1, wherein the cross sectional image is an optical coherence tomography (OCT) image, the cross-sectional imaging system being an OCT imaging system.

11. The method of claim 1, multiple disease locations are determined in the image plane of the cross-sectional image, and a geometric voting algorithm is applied to the multiple disease locations to generate the annotation data based on at least one of: a severity level assigned to each disease location in the cross-sectional image, and a depth of each disease location within or behind the retina.

12. The method of claim 1, applied to multiple conventional retina images and respective associated cross-sectional images, to generate respective annotation data for the multiple conventional retina images, wherein the multiple conventional retina images and their annotation data are used to train an image processing model to identify disease regions in conventional retina images, the multiple conventional retina images used as training inputs and their respective annotation data providing training ground truth, wherein the training inputs do not include the cross-sectional images.

13. The method of claim 12, wherein the training inputs additionally comprise associated patient data.

14. An image processing system comprising:
   an input configured to receive a conventional retina image; and
   one or more processors configured to apply a trained image processing model to the conventional retina image, in order to identify at least one disease location therein, the image processing model trained in accordance with claim 12.

15. A computer program embodying an image processing model, trained in accordance with claim 12.

* * * * *